(12) United States Patent
Adler et al.

(10) Patent No.: US 11,864,990 B2
(45) Date of Patent: Jan. 9, 2024

(54) BIORESORBABLE CORNEAL IMPLANTS

(71) Applicant: Avedro, Inc., Waltham, MA (US)

(72) Inventors: Desmond Christopher Adler, Bedford, MA (US); David Usher, Waltham, MA (US)

(73) Assignee: AVEDRO, INC., Waltham, MA (US)

( * ) Notice: Subject to any disclaimer, the term of this patent is extended or adjusted under 35 U.S.C. 154(b) by 949 days.

(21) Appl. No.: 16/801,735

(22) Filed: Feb. 26, 2020

(65) Prior Publication Data
US 2020/0268505 A1 Aug. 27, 2020

Related U.S. Application Data

(60) Provisional application No. 62/810,635, filed on Feb. 26, 2019.

(51) Int. Cl.
*A61F 2/14* (2006.01)
*A61L 27/24* (2006.01)
*A61L 27/56* (2006.01)

(52) U.S. Cl.
CPC ............ *A61F 2/142* (2013.01); *A61F 2/145* (2013.01); *A61L 27/24* (2013.01); *A61L 27/56* (2013.01); *A61F 2210/0004* (2013.01); *A61L 2300/414* (2013.01)

(58) Field of Classification Search
CPC .. A61F 2/142; A61F 2/145; A61F 2210/0004; A61L 27/24; A61L 27/56; A61L 2300/414; A61L 27/18; A61L 27/50; A61L 27/54; A61L 27/58; A61L 2300/606; A61L 2430/16
See application file for complete search history.

(56) References Cited

U.S. PATENT DOCUMENTS

| | | | | |
|---|---|---|---|---|
| 4,715,858 A | * | 12/1987 | Lindstrom | A61F 2/15 427/2.24 |
| 5,632,773 A | * | 5/1997 | Graham | A61F 2/145 523/108 |
| 5,634,943 A | * | 6/1997 | Villain | C08G 65/32 623/5.11 |
| 5,722,971 A | * | 3/1998 | Peyman | A61F 2/142 606/17 |
| 9,878,066 B2 | | 1/2018 | Stockman et al. | |
| 2006/0034891 A1 | | 2/2006 | Lawin et al. | |
| 2009/0222086 A1 | * | 9/2009 | Lui | C12N 5/0068 424/428 |
| 2011/0052695 A1 | | 3/2011 | Jiang et al. | |
| 2011/0111031 A1 | | 5/2011 | Jiang et al. | |
| 2013/0158342 A1 | | 6/2013 | Chan et al. | |
| 2014/0142200 A1 | | 5/2014 | Duan et al. | |

(Continued)

*Primary Examiner* — Yashita Sharma
(74) *Attorney, Agent, or Firm* — K&L Gates LLP

(57) ABSTRACT

Systems and methods employ bioresorbable corneal implants to treat corneal ectatic disorders and/or refractive errors. The corneal implants may be formed from a porous microstructure that can encourage the proliferation of endogenous keratocytes. As such, the corneal implants act as tissue scaffolds that promote tissue growth to increase the biomechanical stability and/or change the shape of the cornea. Over time, the corneal implants may resorb via hydrolysis or enzymatic breakdown, negating the risks of inflammation, scarring, or foreign body response. The corneal implants may also employ drug coating(s) to promote tissue growth.

14 Claims, 2 Drawing Sheets

(56) References Cited

U.S. PATENT DOCUMENTS

| | | |
|---|---|---|
| 2015/0071871 A1 | 3/2015 | Griffith et al. |
| 2016/0129044 A1 | 5/2016 | Alió y Sanchez et al. |
| 2016/0144069 A1 | 5/2016 | Cho et al. |
| 2016/0151538 A1 | 6/2016 | Kaplan et al. |
| 2017/0049924 A1 | 2/2017 | Stockman et al. |
| 2018/0036453 A1 | 2/2018 | Kaplan et al. |
| 2018/0177718 A1 | 6/2018 | Garcia et al. |
| 2018/0228599 A1 | 8/2018 | Elisseeff et al. |
| 2018/0263756 A1 | 9/2018 | Shiuey |
| 2019/0269826 A1* | 9/2019 | Peyman .................. A61F 2/148 |

* cited by examiner

BIORESORBABLE CORNEAL IMPLANTS

CROSS REFERENCE TO RELATED APPLICATIONS

This application claim priority to, and benefit of, U.S. Provisional Patent Application Ser. No. 62/810,635, filed Feb. 26, 2019, the contents of these applications being incorporated entirely herein by reference.

BACKGROUND

Field

The disclosed subject matter pertains generally to corneal treatments, and more particularly, to systems and methods that employ bioresorbable corneal implants that act as tissue scaffolds to promote tissue growth that increases biomechanical stability of the cornea and/or changes the shape of the cornea.

Description of Related Art

Corneal ectatic disorders, or corneal ectasia, are a group of noninflammatory eye disorders characterized by bilateral thinning of the central, paracentral, or peripheral cornea. For instance, keratoconus is a degenerative disorder of the eye in which structural changes within the cornea driven by a combination of genetic and environmental factors cause the cornea to thin/weaken and change to an abnormal conical shape.

Disorders, such as myopia, hyperopia, or astigmatism, involve refractive errors caused by abnormal corneal shape.

SUMMARY

According to aspects of the present disclosure, systems and methods employ bioresorbable corneal implants to treat corneal ectatic disorders and/or refractive errors. The corneal implants may be formed from a porous microstructure that can encourage the proliferation of endogenous keratocytes. As such, the corneal implants act as tissue scaffolds that promote tissue growth to increase the biomechanical stability and/or change the shape of the cornea. Over time, the corneal implants may resorb via hydrolysis or enzymatic breakdown, negating the risks of inflammation, scarring, or foreign body response. The corneal implants may also employ drug coating(s) to promote tissue growth.

According to an example embodiment, a corneal implant includes a body formed from a material that is configured to resorb into tissue of a cornea over a period of time, the body having an anterior surface and a posterior surface. The corneal implant includes a first drug coating applied to an anterior surface of the body and/or a second drug coating applied to a posterior surface of the body. The first drug coating or the second drug coating is formulated at least to promote keratocyte proliferation in and around the body.

In the example embodiment above, the body may include a porous microstructure that promotes keratocyte mobility from the native stromal tissue surrounding the body.

In the example embodiment above, the material may be configured to resorb into the corneal tissue over a period of time by hydrolytic or enzymatic action.

In the example embodiment above, the body may be formed from a bioresorbable polymer. The bioresorbable polymer may include polylactide (PLA), polycaprolactone (PCL), or poly(lactide-co-glycolide) (PLGA).

In the example embodiment above, the material may be configured to resorb into the corneal tissue over a plurality of weeks.

In the example embodiment above, the first drug coating or the second drug coating may elute over the period of time for resorption of the body.

In the example embodiment above, the first drug coating or the second drug coating may include a growth factor.

In the example embodiment above, the first drug coating or the second drug coating may include a plurality of drugs that are layered to allow the plurality of drugs to elute in an order. The first drug coating or the second drug coating may include a growth factor and a cross-linking agent layered to allow the growth factor to elute prior to the cross-linking agent, the cross-linking agent generating chemical cross-links between native collagen fibers and collagen formed in and around the body.

In the example embodiment above, the body may have a neutral shape that does not impart changes to a curvature of an anterior surface of the cornea.

In the example embodiment above, the body may be shaped to impart a refractive change in the cornea. The anterior surface of the body may be convex to increase curvature of an anterior surface of the cornea. The anterior surface of the body may be concave to decrease curvature of an anterior surface of the cornea.

Figure 1:
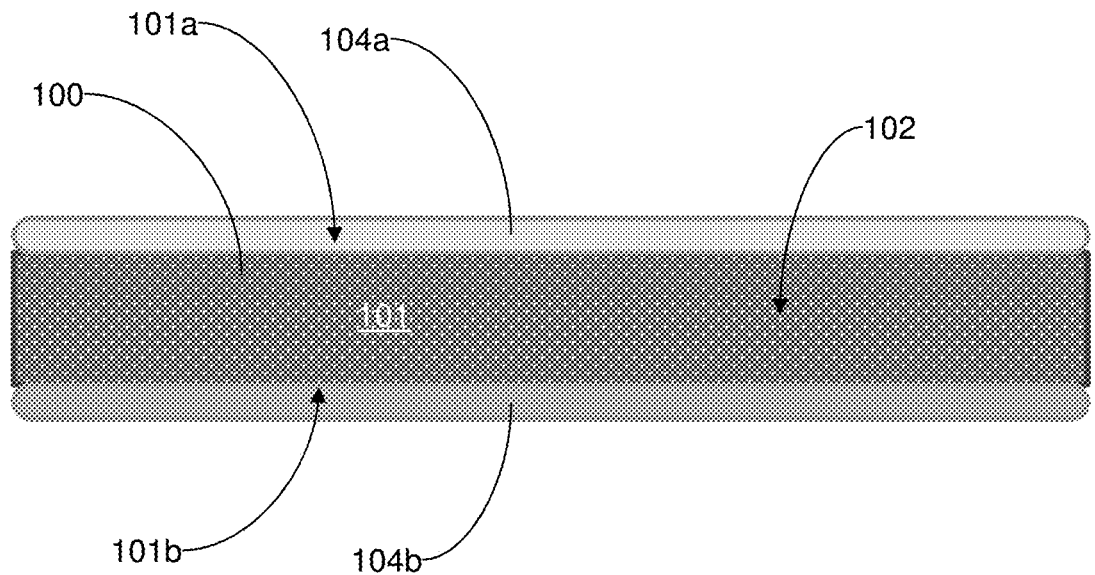
FIG. 1 illustrates an example bioresorbable corneal implant, according to aspects of the present disclosure.

While the present disclosure is susceptible to various modifications and alternative forms, a specific embodiment thereof has been shown by way of example in the drawings and will herein be described in detail. It should be understood, however, that it is not intended to limit the present disclosure to the particular forms disclosed, but on the contrary, the intention is to cover all modifications, equivalents, and alternatives falling within the spirit of the present disclosure.

DESCRIPTION

Keratoconus is characterized by progressive thinning and weakening of the cornea. Corneal cross-linking treatments can effectively arrest the progression of keratoconus in a large majority of cases. Some patients, however, are not candidates for corneal cross-linking treatments due to contraindications, such as thin corneas (less than approximately 400 μm in thickness), prior herpetic infection, or pregnancy. Therefore, there exists a need for alternate treatments in certain patient groups.

According to aspects of the present disclosure, a bioresorbable corneal implant may be employed to restore biomechanical stability to an eye experiencing a corneal ectatic disorder, such as keratoconus. Additionally or alternatively, the corneal implant may be employed to induce controlled shape changes to a cornea to impart a corrective refractive change.

FIG. 1 illustrates an example bioresorbable corneal implant 100. The corneal implant 100 includes a body 101 that is formed from a material that can fully resorb by hydrolytic or enzymatic action in the cornea over a period of time. Thus, the corneal implant 100 is not intended to act as a permanent replacement for corneal tissue. For instance, the corneal implant 100 may be formed from a bioresorbable polymer such as polylactide (PLA), polycaprolactone (PCL), poly(lactide-co-glycolide) (PLGA), or similar material. The resorption rate of the corneal implant 100 may be controlled via selection of the material (e.g., by the copolymer ratios of PLGA) or by aspects of the manufacturing process.

The bioresorbable polymer may have high optical transmissivity in the visible wavelength range (i.e., approximately from 400 nm to approximately 700 nm), so the corneal implant 100 does not impair the vision of the patient before the corneal implant 100 resorbs completely. In general, the corneal implant 100 may be formed from a transparent material, which minimizes transient visual impact.

The corneal implant 100 has a combination of mechanical and chemical properties that promotes natural keratocyte proliferation in and around the corneal implant 100. In particular, the corneal implant 100 includes a porous microstructure 102 (e.g., a pattern of holes) that promotes keratocyte mobility from the native stromal tissue surrounding the corneal implant 100. For instance, a pattern of holes can be produced by electrospinning when the corneal implant 100 is formed, or by laser drilling during a secondary operation. As such, the corneal implant 100 acts as a tissue scaffold that promotes the growth of corneal tissue which stabilizes or reshapes the cornea. The time period for resorption of the corneal implant 100 may be several weeks, for instance, to provide sufficient time for keratocyte growth and collagen production while minimizing the amount of time the corneal implant 100 resides in the cornea.

The corneal implant 100 also includes one or more drug coatings. The drug coatings may be applied on different surfaces of the corneal implant 100. For instance, as shown in FIG. 1, a first drug coating 104a is applied to an anterior surface 101a of the body 101 of the corneal implant 100 and a second drug coating 104b is applied to a posterior surface 101b of the body 101 of the corneal implant 100. When the corneal implant 100 is implanted, the anterior surface 101a of the body faces the anterior surface of the cornea and the posterior surface 101b of the body 101 faces the posterior surface of the cornea. Each coating 104a, b may elute over a defined time period consistent with the expected resorption time of the entire corneal implant 100 (e.g., several weeks). In some cases, the rate of resorption of the corneal implant 100 may be controlled to give sufficient time for the drug coating(s) to fully elute.

In some embodiments, the drug coatings may be formulated to promote keratocyte growth and collagen production. For instance, the drug coatings may include a growth factor. Additionally or alternatively, the drug coatings may generate chemical cross-links between the collagen fibers in the existing stroma and the collagen formed within the scaffold provided by the corneal implant 100. The cross-linking can further enhance biomechanical properties of the cornea.

Each drug coating 104a, b may include one or more drugs. When a drug coating includes more than one drug, the plurality of drugs may be mixed together in a single layer of the drug coating. Alternatively, the plurality of drugs may be layered in series so that the drug in one layer elutes prior to the drug in another layer below (in an order). For instance, in one embodiment, a drug coating may include a growth factor as well as a cross-linking agent (e.g., riboflavin), where the growth factor and the cross-linking agent are applied in respective layers. As such, the growth factor elutes prior to the cross-linking agent. Advantageously, applying the drugs in such layers allows keratocytes to fill in the scaffold provided by the corneal implant 100 and produce new collagen before exposing the corneal tissue to the cross-linking agent. Indeed, the cross-linking agent may be partially toxic to the keratocytes in the initial proliferation.

Figure 2:
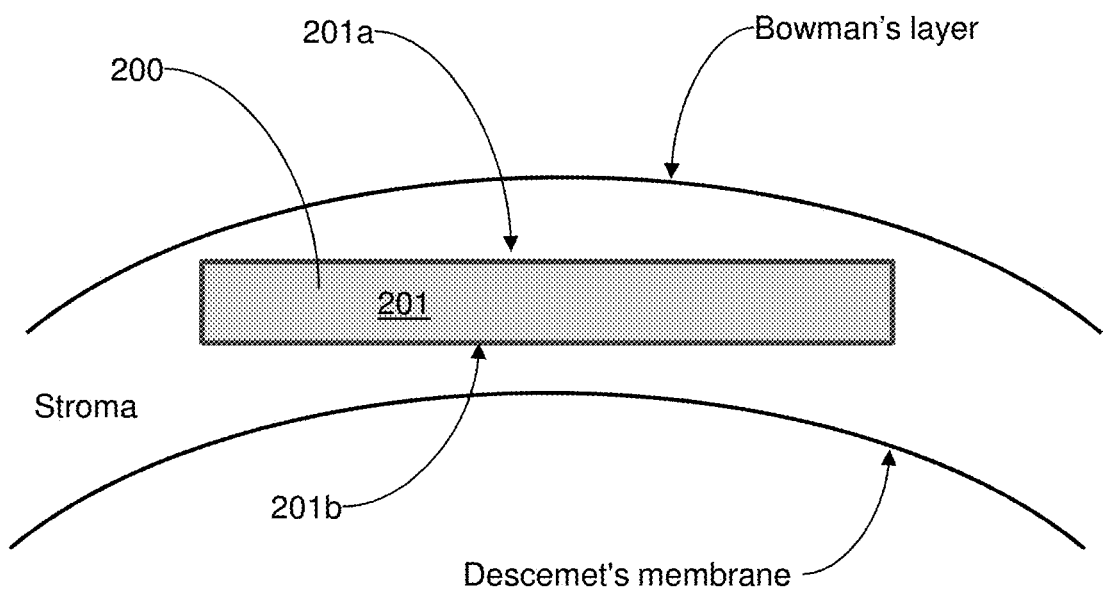
FIG. 2 illustrates an example bioresorbable corneal implant that is neutrally shaped in order to restore corneal thickness without imparting deliberate changes to curvature of the anterior surface of the cornea, according to aspects of the present disclosure.

FIG. 2 illustrates an example bioresorbable corneal implant 200 that can provide a tissue scaffold as described above. The corneal implant 200 has a body 201 that is neutrally shaped in order to restore corneal thickness without imparting deliberate changes to curvature of the anterior surface of the cornea. Additionally, the thickness of the corneal implant 200 between an anterior surface 201a and a posterior surface 201b of the body 201 is selected to avoid disruptions to Bowman's layer and Descemet's membrane.

Figure 3:
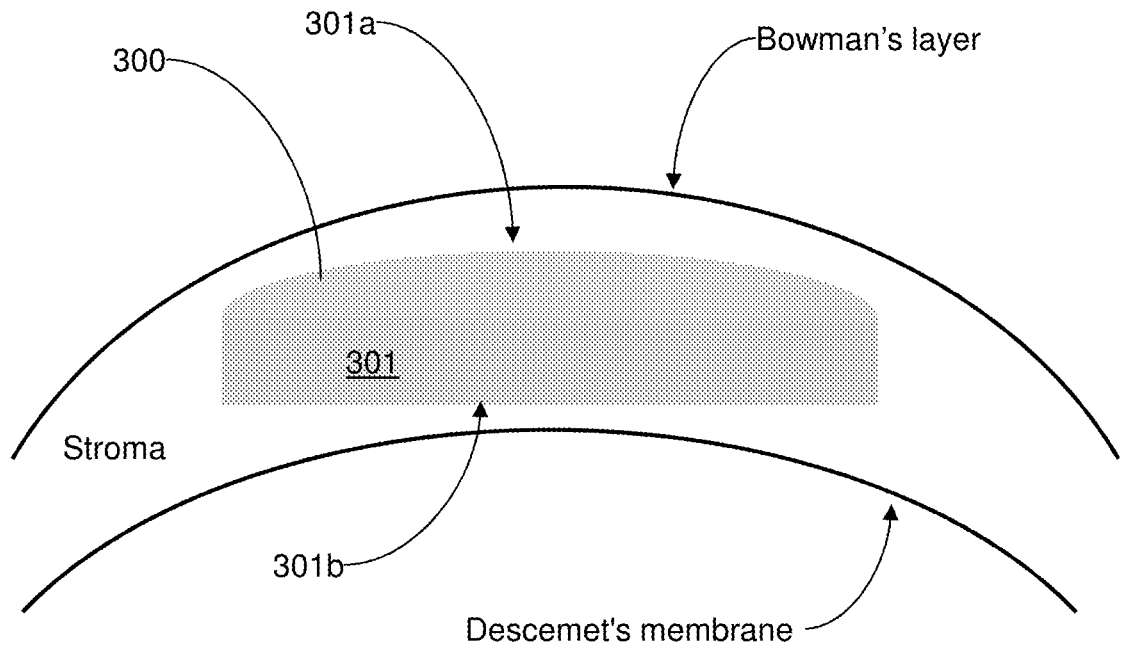
FIG. 3 illustrates another example bioresorbable corneal implant including an anterior surface with a convex shape, which can steepen the anterior surface of the cornea while also restoring corneal thickness, according to aspects of the present disclosure.
Figure 4:
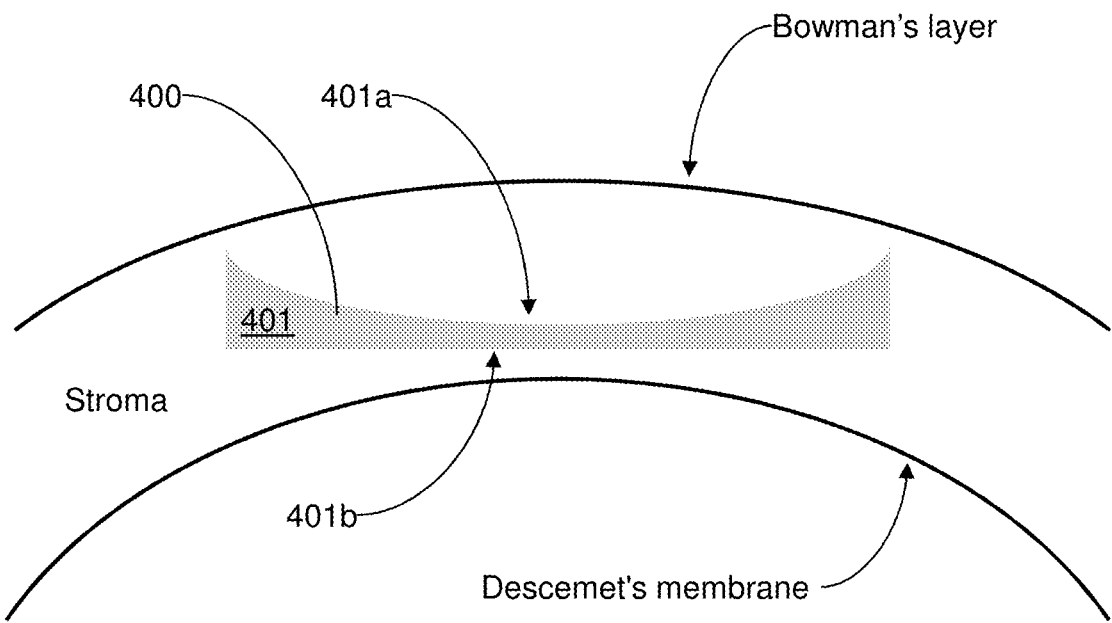
FIG. 4 illustrates yet another example bioresorbable corneal implant including an anterior surface with a concave shape, which can flatten the anterior surface of the cornea while also restoring corneal thickness, according to aspects of the present disclosure.

As shown in FIGS. 3 and 4, however, the surface profiles and thicknesses of bioresorbable corneal implants may be customized to individual patients and/or customized to additionally impart a refractive change in the cornea. For instance, FIG. 3 illustrates an example bioresorbable corneal implant 300 that can provide a tissue scaffold as described above. The corneal implant 300 includes a body 301 with an anterior surface 301a and a posterior surface 301b. The anterior surface 301a has a convex shape, which can steepen the anterior surface of the cornea (increase anterior surface curvature) while also restoring corneal thickness. The steepening of the anterior surface of the cornea increases the focusing power of the cornea and can be used to impart a hyperopic correction to the vision of the patient in addition to increasing corneal thickness. As such, the corneal implant 300 can be employed to treat hyperopia and/or presbyopia.

Alternatively, FIG. 4 illustrates an example bioresorbable corneal implant 400 that can provide a tissue scaffold as described above. The corneal implant 400 includes a body 401 with an anterior surface 401a and a posterior surface 401b. The anterior surface 401a has a concave shape, which can flatten the anterior surface of the cornea (decrease anterior surface curvature) while also restoring corneal thickness. The flattening of the anterior surface of the cornea decreases the focusing power of the cornea and can be used to impart a myopic correction to the vision of the patient in addition to increasing corneal thickness. As such, the corneal implant 300 can be employed to treat myopia.

The thickness of the corneal implants (between anterior and posterior surfaces) can be adjusted during manufacturing or via secondary operations (e.g., laser processing) to accommodate the corneal thickness of the individual patient. For instance, a patient with a thin cornea of approximately 350 μm may require a corneal implant with a thickness of only approximately 100 or 150 μm, whereas a patient with a corneal thickness of approximately 500 um may require a corneal implant with a thickness of approximately 250 or 300 μm. Thus, the range of thicknesses for the corneal implants may range from approximately 100 to approximately 300 μm.

In general, mechanical properties of the corneal implants can be adjusted to achieve the desired combination of visible light transmission, cellular proliferation, and drug delivery characteristics.

Advantageously, corneal implants according to the present disclosure resorb over time and only reside in the cornea temporarily. The corneal implants are therefore thinner than the recipient cornea and do not need to possess the mechanical properties (e.g. tensile strength) or optical properties (e.g., long-term transmissivity) for permanent residence in the cornea.

While the present disclosure has been described with reference to one or more particular embodiments, those skilled in the art will recognize that many changes may be made thereto without departing from the spirit and scope of the present disclosure. Each of these embodiments and obvious variations thereof is contemplated as falling within the spirit and scope of the present disclosure. It is also contemplated that additional embodiments according to aspects of the present disclosure may combine any number of features from any of the embodiments described herein.

What is claimed is:

1. A corneal implant, comprising:
   a body formed from a material that is configured to resorb into tissue of a cornea over a period of time, the body having an anterior surface and a posterior surface; and
   a first drug coating applied to an anterior surface of the body and/or a second drug coating applied to a posterior surface of the body, the first drug coating or the second drug coating formulated at least to promote keratocyte proliferation in and around the body,
   wherein the first drug coating or the second drug coating includes a plurality of drugs that are layered to allow the plurality of drugs to elute in an order, and
   wherein the first drug coating or the second drug coating include a growth factor and a cross-linking agent layered to allow the growth factor to elute prior to the cross-linking agent, the cross-linking agent generating chemical cross-links between native collagen fibers and collagen formed in and around the body.

2. The corneal implant of claim 1, wherein the body includes a porous microstructure that promotes keratocyte mobility from the native stromal tissue surrounding the body.

3. The corneal implant of claim 1, wherein the material is configured to resorb into the corneal tissue over a period of time by hydrolytic or enzymatic action.

4. The corneal implant of claim 1, wherein the body is formed from a bioresorbable polymer.

5. The corneal implant of claim 4, wherein the bioresorbable polymer includes polylactide (PLA), polycaprolactone (PCL), or poly(lactide-co-glycolide) (PLGA).

6. The corneal implant of claim 1, wherein the material is configured to resorb into the corneal tissue over a plurality of weeks.

7. The corneal implant of claim 1, wherein the first drug coating or the second drug coating elute over the period of time for resorption of the body.

8. The corneal implant of claim 1, wherein the first drug coating or the second drug coating include a growth factor.

9. The corneal implant of claim 1, wherein the body has a neutral shape that does not impart changes to a curvature of an anterior surface of the cornea.

10. The corneal implant of claim 1, wherein the body is shaped to impart a refractive change in the cornea.

11. The corneal implant of claim 10, wherein the anterior surface of the body is convex to increase curvature of an anterior surface of the cornea.

12. The corneal implant of claim 10, wherein the anterior surface of the body is concave to decrease curvature of an anterior surface of the cornea.

13. The corneal implant of claim 1, wherein the corneal implant has a thickness of approximately 100 um to approximately 300 gm.

14. The corneal implant of claim 1, wherein the body has optical transmissivity in a wavelength range from approximately 400 nm to approximately 700 nm.

* * * * *